United States Patent [19]

Melzer et al.

[11] Patent Number: 5,406,940
[45] Date of Patent: Apr. 18, 1995

[54] MEDICAL INSTRUMENT FOR CREATING A TISSUE CANAL

[75] Inventors: Andreas Melzer, Wiesbaden; Gerhard Buess, Tübingen, both of Germany

[73] Assignee: Olympus Winter & Ibe GmbH, Hamburg, Germany

[21] Appl. No.: 111,628

[22] Filed: Aug. 25, 1993

[30] Foreign Application Priority Data

Sep. 2, 1992 [DE] Germany .................. 42 29 310.3

[51] Int. Cl.6 .................. A61B 1/06; A61B 17/32
[52] U.S. Cl. .................. 128/6; 606/180
[58] Field of Search .............. 606/180, 167, 184, 185, 606/7; 128/4, 6

[56] References Cited

U.S. PATENT DOCUMENTS

| | | | |
|---|---|---|---|
| 3,961,621 | 6/1976 | Northeved | 128/6 |
| 4,254,762 | 3/1981 | Yoon | 128/4 |
| 4,269,192 | 5/1981 | Matsuo | 128/6 |

*Primary Examiner*—Tamara L. Graysay
*Attorney, Agent, or Firm*—Walter C. Farley

[57] ABSTRACT

A surgical instrument for creating a tissue canal in which to seat a sleeve has a shaft tube with a knife blade at its distal end to form an incision and an insert to transform the incision into the tissue canal. The knife blade is formed as an axially projecting portion of the distal edge of the shaft tube and has a ground edge for cutting in the circumferential direction of the shaft tube. The insert is slidable mounted in the shaft tube and has a distal blunt end located adjacent the distal end of the shaft tube.

8 Claims, 4 Drawing Sheets

MEDICAL INSTRUMENT FOR CREATING A TISSUE CANAL

FIELD OF THE INVENTION

The invention concerns a medical or surgical instrument for forming a canal or channel through tissue.

BACKGROUND OF THE INVENTION

Instruments of this general type are used in the course of laparoscopic penetration into, for example, the abdominal cavity. In such penetration, first the abdominal wall is pierced in a suitable area using a thin cannula and then the abdominal space is filled through the cannula with gas.

Thereafter, one or more apertures are created in the abdominal wall above the target of intervention. So-called trocar sleeves are inserted into these apertures. These trocar sleeves are fitted with gas valves and through them the required laparoscopic instruments can be inserted during the intervention into the abdominal cavity.

To assure suitable hermetic sealing, the apertures made in the abdominal wall must have as constant as possible a cross-section over their length. Such apertures allow snug seating of the trocar sleeves with gas-tight sealing.

As a rule, so-called trocars having triangular ground cutting edges at their ends are used to make the apertures. The trocars are pushed through the abdominal wall and the aperture so made is expanded, where called for, by means of dilators.

Disadvantageously, however, the surgeon must exert a relatively large force on the trocar to pierce the abdominal wall. Fine control of the piercing or fine control of the advance is impossible. This may lead to fatal consequences if the surgeon selects a part of the abdominal wall for piercing that may cling to organs.

Some surgeons prefer opening the abdominal wall in the manner of the so-called "mini-laparoscopy" in which a scalpel is made to enter the abdominal wall in short and carefully guided cuts. This technique only calls for slight force, but it has the drawback that the aperture so made is comparatively undefined and thereby may be unsuitable to hermetically seat a trocar sleeve.

Reference is made to the German patent document 34 03 962 C2 which discloses an instrument of the above type to create a tissue canal and which comprises a shaft bearing at its distal end an axially cutting knife. When the shaft is advanced through the tissue, a plane cutting surface of constant width is generated over the entire length of advance and, by laterally displacing the tissue zones adjoining the cutting surface, can be widened into the desired canal without requiring force. However, this instrument also raises the question whether the canal so made can ensure hermeticity for an installed sleeve.

SUMMARY OF THE INVENTION

Accordingly, an object of the present invention is to provide an instrument for making a defined tissue canal with minimal application of force with maximal reliability.

This object is achieved by an instrument having a knife blade formed by an axially projecting zone of a distal tube edge of a shaft tube. The knife blade comprises a ground or sharpened surface for making an incision in the circumferential direction of the shaft tube. An insert is mounted in the shaft tube with the distal end of the tube located approximately even with the distal end of the insert. The distal end of the blade projects beyond the insert.

The operation of the instrument, is as follows. To provide access to the abdominal space, the instrument of the invention is placed with the blade against the abdominal wall and is rotated about its longitudinal axis in alternating directions. The blade knife thereby incises the abdominal wall over a defined angular excursion. The angular excursion is preferably less than 360° to avoid detaching tissue parts. The angular excursion may easily be less than 180°. The undetached tissue of the remaining sector is easily pushed to the side by the distal end of the insert during instrument penetration and is shaped into a good sealing canal.

As a result, the instrument of the invention allows controlled penetration of the abdominal wall in a simple manner and with minimal application of force. The smooth cut surface produced by the blade together with the tissue displaced by the insert sub-tends a defined canal.

If during penetration of the tissue an obstacle is encountered that must be bypassed, then the distal end of the instrument of the invention can be shifted to the side by one tube diameter by being rotated about the blade tip. In this manner it is possible to steer to a limited extent the instrument of the invention even after penetration of a tissue. The size of the possible change in position depends on the resistance of the already penetrated tissue layers.

If a canal must be made by the instrument of the invention in tissue that also can be pierced by a blunt means, then rotary cutting is not mandatory. The instrument instead may be merely forced in, the blade being used as a guide accessory for preventing sideways slippage. Therefore, as called for, alternating tissue layers may be pierced with or without cutting.

Accordingly, the instrument of the invention is suitable not only for making apertures in the abdominal wall, for example, but can be widely used wherever a tissue canal must be made.

In a specific embodiment, the distal end of the blade may be made slanting. Such a blade is especially easily deposited and held in place on a defined spot on the abdominal wall. Alternatively, the blade may have a round distal end. Such a blade shape makes possible especially gentle cuts.

Advantageously the blade is formed so as to be able to cut in both directions of rotation, and advantageously the tip also is capable of cutting.

An insert is provided to temporarily displace the cut tissue layers, this insert comprising at its end a slant away from the blade tip. Such an insert displaces the tissue in a particularly gentle manner from the cutting surface.

As discussed above, some tissue may be pierced in blunt manner, that is, a cutting tool is not mandatory. This eventuality is met in especially advantageous manner by an embodiment in which either the slanting end of the insert or the blade is selectively moved into a distally projecting position. For instance, by simply actuating a manual switch, the surgeon is able to select one of the functions. If for instance he encounters skin, connective tissue or sinews, the knife blade will be used, otherwise, in softer tissues, the insert may be moved into an advanced distal position and the tissue may be pierced bluntly. This embodiment allows an especially gentle generation of a tissue canal with little injury.

If the shaft tube is non-rotationally affixed to the overall instrument, then cutting must be implemented by rotating the entire instrument. Advantageously, however, the shaft tube is rotatable relative to the remaining instrument and therefore rotary cutting can be done without having to rotate the entire instrument as a unit.

In the event the instrument of the invention must be used in the cutting mode, the shaft tube must be rotated about its longitudinal axis in alternating directions and through a defined angular excursion. However manual rotation is difficult for the surgeon. Therefore a further advantageous embodiment of the invention provides that a drive be fitted to the instrument which rotates the shaft tube alternatingly in opposite directions about its longitudinal axis. In a further advantageous embodiment, this drive also can be preset for several different angular excursions of the shaft axis and hence of the tissue cut. Illustratively, the drive may be an electric motor or a pneumatic actuator.

The above embodiments advantageously allow the surgeon to set the cutting function by merely actuating the drive so as to preserve his total concentration for guiding the instrument through the tissue. Activation and deactivation of the drive can be linked to the implementation of longitudinal displacement and in an especially simple manner in an instrument wherein the blunt insert end or the blade can be selectively moved into a distally projecting position. Upon advancing the blade into the cutting position, the drive is actuated. Reversely, the drive is deactivated when the insert is being advanced.

The above described embodiments of the invention concern an instrument allowing tissue penetration with minimal force; however, this penetration is performed blindly. A further especially advantageous embodiment comprises an insert with optics therein. When using this embodiment, the instrument path through the tissue layers can be checked optically. The optical fibers illuminate through the tissue structures. Any vessels in the way of the instruments are easily recognized and by-passed. In particular the penetration of the abdominal wall can be selected in such a manner that no organs underneath will be injured. The peritoneum being translucent, growths can be spotted before penetration. In the presence of optical checking, the instrument can be steered into a growth-free zone of the abdominal cavity.

A spacer such as a glass block may be provided in front of the optics to keep the tissue in front of the instrument at any required imaging distance.

In addition, optics can be used which allow focusing even when the tissue makes contact with the front surface of the objective. Such optics allow especially clear imaging with least light losses.

In particular with respect to the last embodiment, optical checking also can be carried out in problem-free manner when penetrating soft tissue with distally advanced insert.

A problem however arises in this regard, namely that as a rule commonplace endoscopes are such that they will focus not on objects directly on the front surface of the objective but some distance away from said surface. For reasons of economy, it is desirable to use such endoscope optics also with the instrument of the invention. A further advantageous embodiment of the invention provides an adapter mounted on the ocular when using such standard optics for shifting the focal length so that focusing on the front (exterior) surface of the objective is thereby possible.

In a further embodiment, the adapter can be toggled between two focal lengths. When one focal length is set, imaging takes place on the front surface of the objective. When setting the other focal length, objects a selected distance from the objective are imaged. Such an instrument can be optimally matched to the various conditions of observation. During piercing the imaging is directly at the objective. Following piercing of the abdominal wall and penetration of the abdominal cavity, the other focal length may be switched on and the objects may be viewed from a distance as in the standard optics.

The insert and the shaft tube are preferably mutually rotatable. The surgeon is thus able to rotate the shaft into a circularly cutting motion of the blade without displacing the insert. This is especially advantageous when the insert is fitted with optics, because in that case the image does not rotate.

BRIEF DESCRIPTION OF THE DRAWINGS

The invention is described below with reference to the following figures showing preferred embodiments wherein.

DESCRIPTION OF THE PREFERRED EMBODIMENTS

Figure 1:
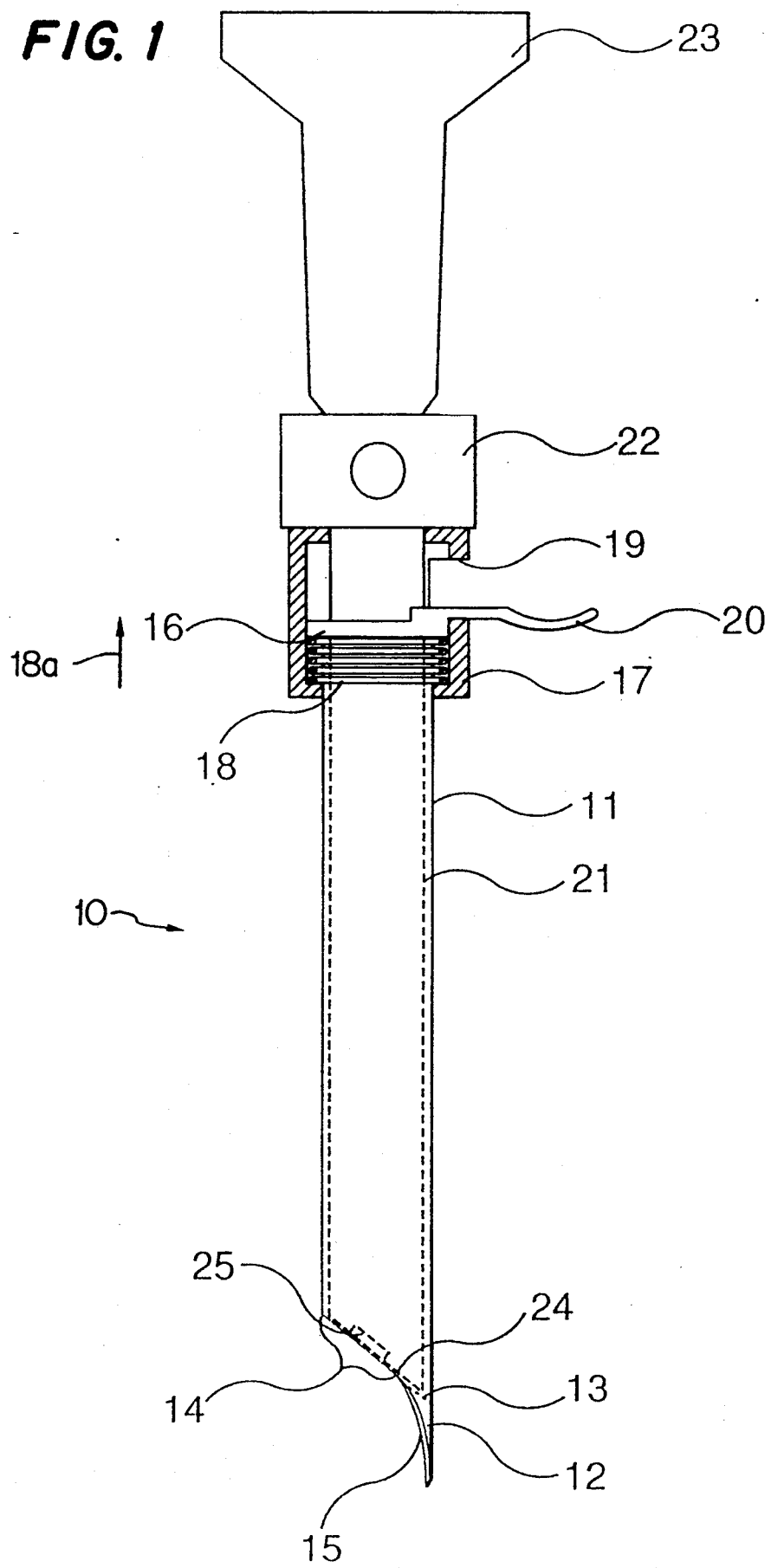
FIG. 1 is a front elevation of an embodiment of an instrument in accordance with the invention in which an insert and a shaft tube rest against one another in a circularly and axially displaceable manner and wherein the blade is shown in an advanced position.

FIG. 1 shows an instrument indicated generally at 10 having a shaft tube 11 formed or fitted with a blade 12 at its distal end. Blade 12 extends around part of the tube circumference and protrudes in the direction of the shaft axis. The portion 14 of the distal end of the shaft tube not having the blade is slanted, a continuation of the plane containing this slanted surface being indicated by line 13. Blade 12 is clearly shown projecting beyond plane 13 at the front edge of the tube. The dashed line 13 denotes an essentially planar extension of the portion 14 of the tube front edge resembling a straight cutting surface in the manner of a conventional cannula end, the blade 12 projecting from the straight cutting surface so formed.

The blade 12 has a ground or sharpened cutting edge, not shown, on at least one of its side edges 15.

An annular shoulder ring 16 having an axially facing shoulder is positioned at the proximal end of shaft tube 11 and a compression spring 18 contained within a cylindrical housing 17 abuts the distally facing shoulder of ring 16. For clarity, housing 17 is shown only in section. Compression spring 18 forces ring 16 in the direction of arrow 18a. A lever 20 is attached to the periphery of ring 16 and extends outside of housing 17 through an aperture 19 in the housing. Using lever 20, shaft tube 11 can be manually displaced against the force of spring 18.

Figure 2:
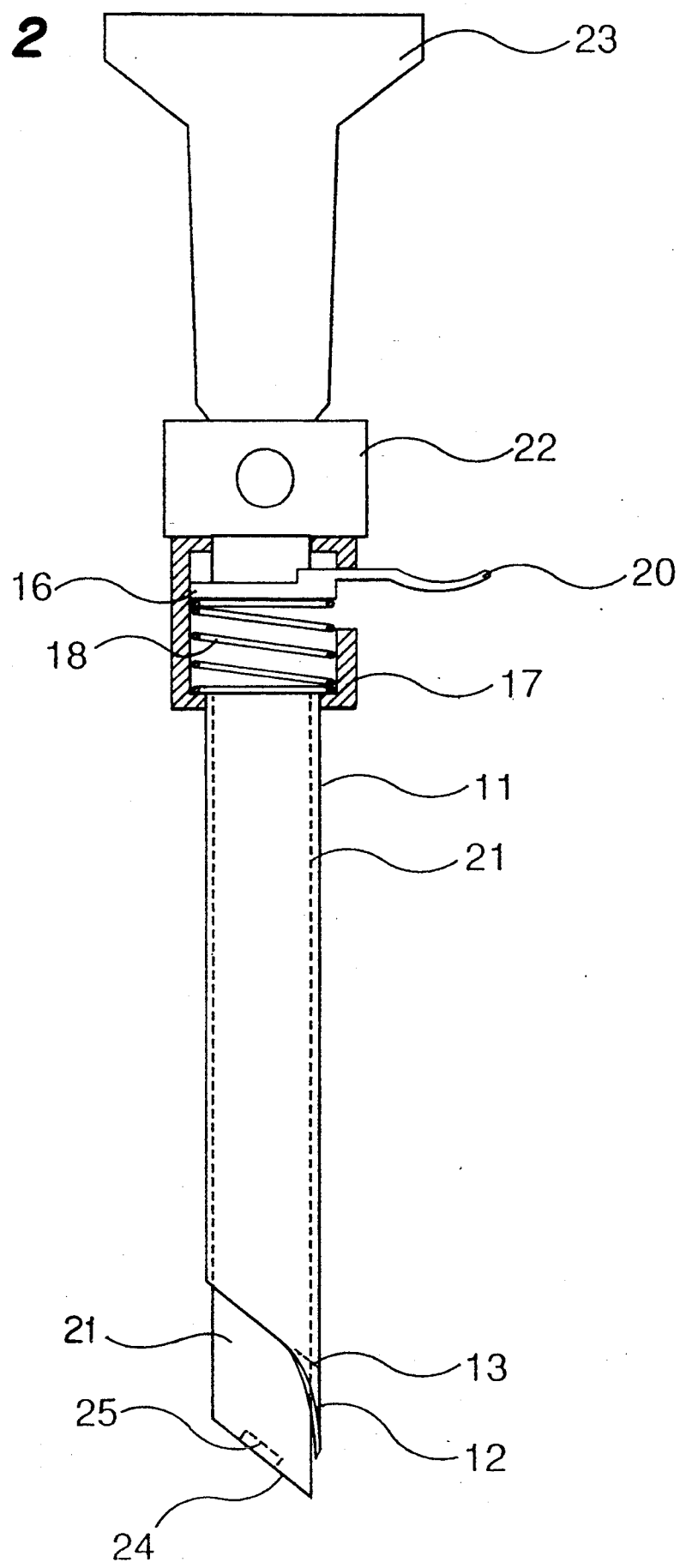
FIG. 2 is a front elevation of the embodiment of FIG. 1 but with the insert in a distally advanced position.

A cylindrical insert 21 is slidably contained within shaft tube 11. In a preferred embodiment, insert 21 and shaft tube 11 are mutually rotatable. As shown in FIGS. 1 and 2, aperture 19 in housing 17 is an arcuate opening having an angular extent sufficient to allow movement of lever 20 over a preselected circumferential range so that by actuating lever 20 it is possible both to axially displace shaft tube 11 and also to rotate it relative to insert 21.

Insert 21 is fixedly held in a clamp 22 mounted on the proximal end of housing 17 and is provided with suitable optics. Insert 21 is fitted with an ocular 23 at its proximal end. An objective 25 is mounted at the distal end 24 of insert 21. As seen in the figures, the distal end 24 of the insert 21 lies in a plane which slants relative to the central axis of the insert so that, when lever 20 is in the center of its arcuate movement, the longest side of the insert is adjacent blade 12 on shaft tube 11 and objective 25 faces away from the blade. As discussed above, optimal displacement of the tissue incised by cutting edge 15 of blade 12 is possible.

FIG. 1 shows blade 12 extending beyond insert 21 in the distally advanced position which can be reached by depressing lever 20 against the force of spring 18. However, if the surgeon wishes to first penetrate the tissue with, the distal end 24 of the insert 21 (that is, in blunt penetration), then lever 20 merely need being released. As shown in FIG. 2, spring 18 then forces ring 16 in the proximal direction and carries shaft tube 11 which is fixed to it. Distal end 24 of insert 21 then is in a distally advanced position relative to blade 12. As already stated above, it is easy to penetrate some tissues with the slanted end 24 of insert 21. It will be especially advantageous in that circumstance that the optics provided in the insert 21 allow focusing on the front surface of objective 25.

Figure 3:
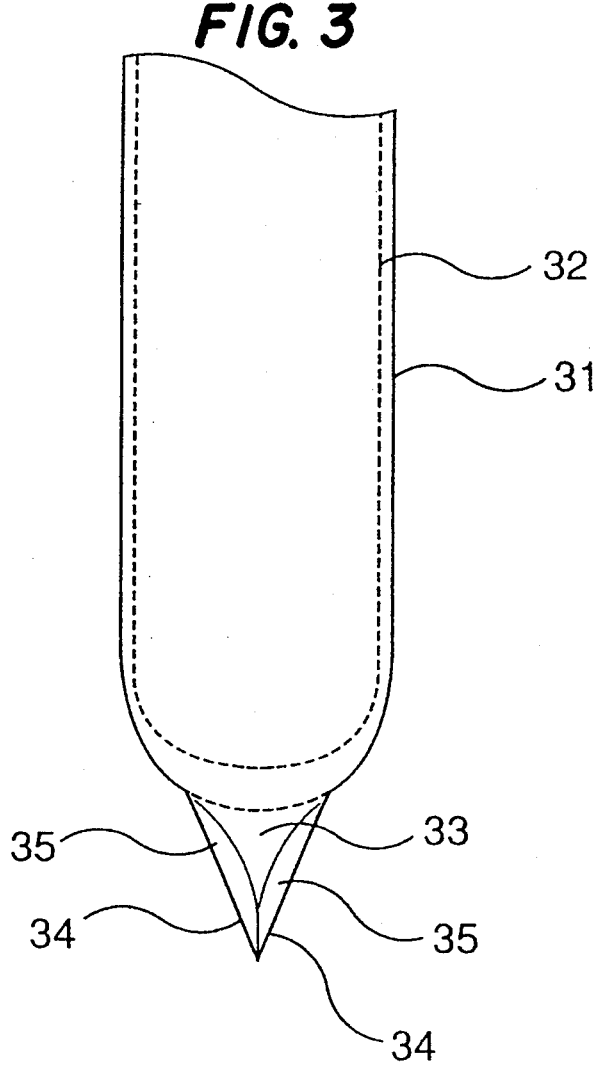
FIGS. 3 and 4 are partial side elevations of further embodiments with different blade shapes.
Figure 4:
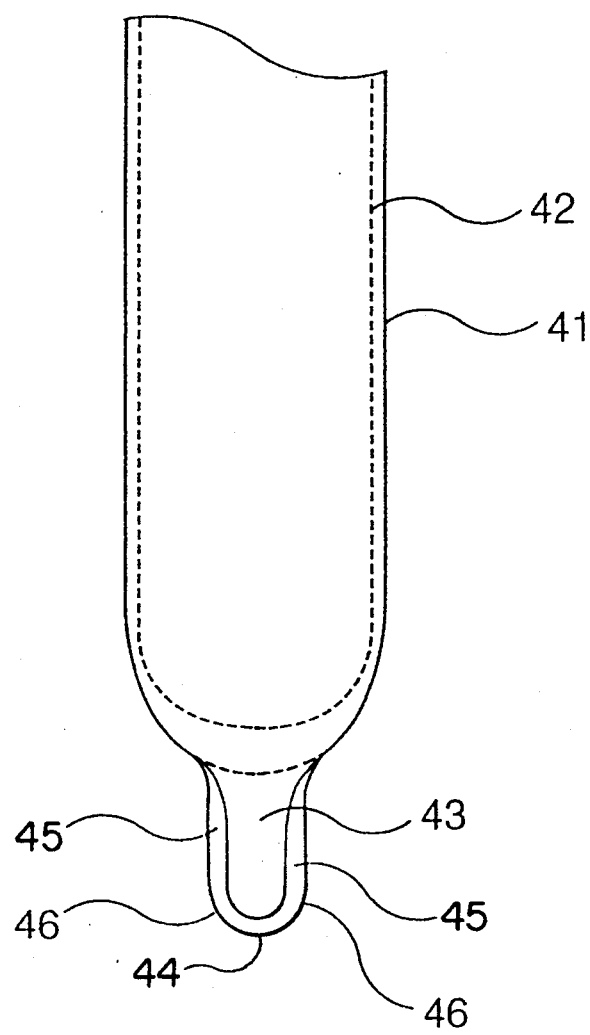

FIGS. 3 and 4 show only the distal end zones of embodiments of the invention in side views.

FIG. 3 shows a shaft tube 31 with an insert 32. A tapered blade 33 (shown in side view) at the distal end of shaft tube 31 has a ground cutting edge 35 at each side edge 34.

The embodiment of FIG. 4 comprises a shaft tube 41 with an insert 42 and with a blade 43 at the distal end of the tube, the distal end 44 of the blade being rounded. A peripherally ground cutting edge 45 extends entirely around the exposed edge of blade 43, from one side edge 46 to the other.

Ultimately the surgical conditions will determine which blade shape and which ground cutting edge is selected. In order to broaden the applicability of the instrument of the invention, the shaft tube may be made detachable. This would allow easy blade exchange.

Variations on the above described embodiments of the invention are possible. With respect to FIG. 1, it will be noted that blade 12 is made to project beyond the front-edge portion 14 of shaft tube 11, portion 14 being slanted relative to the axis of the shaft tube 11. This zone also may be in the form of a curved surface. In special cases, the tube front-edge portion 14 outside blade 12 also might subtend an obtuse angle to the axis of shaft tube 11, or be transverse to said tube.

Once the tissue canal has been made, shaft tube 11 can remain in it in the manner conventional for trocar sleeves and be used as such. When used as a laparoscopy port, a conventional valve must be added to the components shown in FIGS. 1 and 2, for instance inside clamp 22.

When used as a laparoscopy port, however, the blade 12 would interfere because when the end is shaped in such a traumatizing manner located in the body, there is danger of injury.

Preferably therefore the instrument shown in FIGS. 1 and 2 would be used only to create the tissue canal, after which it is removed and replaced by a laparoscopy port. This port can be displaced over shaft tube 11 during the creation of the tissue canal, where called for, by inserting an enlarging intermediate tube with a conical dilating tip.

Figure 5:
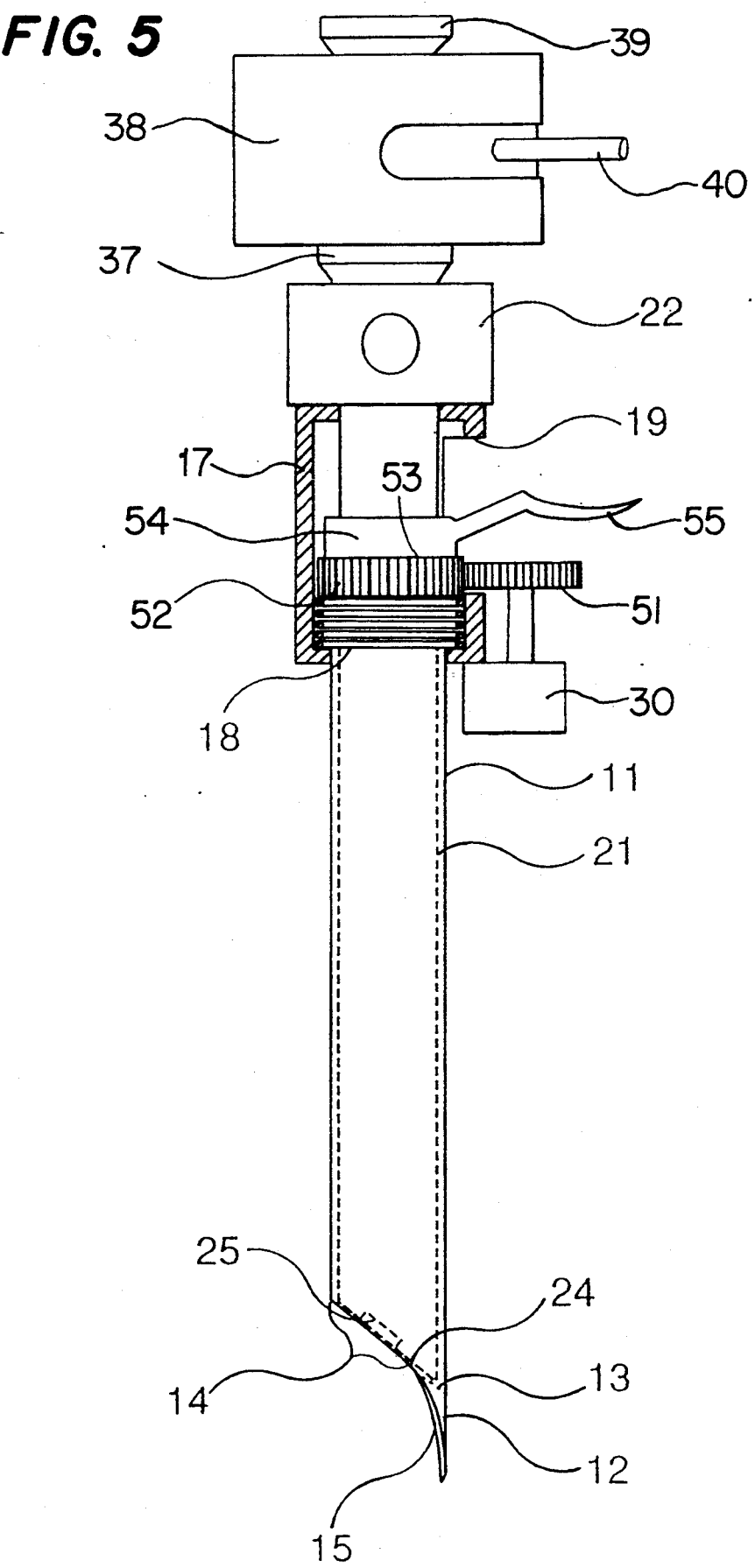
FIG. 5 is a front elevation of another embodiment of an instrument in accordance with the invention with a drive for the shaft tube and an adapter mounted on the ocular.

FIG. 5 shows an embodiment of the invention which is based on the essential features of the embodiment shown in FIG. 1. Therefore congruent features are denoted by the same reference numerals as for the embodiment of FIG. 1. The difference relative to FIG. 1 in the presently discussed embodiment is a drive in the form of an electric motor 30 mounted on housing 17. Through a pinion 51, the electric motor 30 drives a gear 52 rigidly fixed to shaft tube 11. In order to produce alternating rotation, the electric motor can be powered in alternatingly opposite directions or it may be fitted with a reversing gear. FIG. 5 shows that gear 52 has teeth 53 only over part of its circumference. In the embodiment illustrated, shaft tube 11 can therefore be rotated only through a limited angular excursion. Alternatively, teeth also may be provided over the entire circumference of the gear 52, in which case limitation of the angular excursion can be provided by means of suitable conventional control of the electric motor. Gear 52 is displaceably supported in the housing 17 against the force of the spring 18. The gear 52 can be displaced against the spring 18 by means of a slip ring 54 which is axially slidable on insert 21 and is moved by a lever 55.

In the position shown in FIG. 5, slip ring 54 has been displaced by lever 55 in the distal direction so that teeth 53 of gear 52 mesh with the pinion 51 of electric motor 30. When, in this position, lever 55 is released, spring 18 will press gear 52 and slip ring 54 in the proximal direction, disengaging gear 53 from pinion 51. In this manner, the rotational drive of the shaft tube 11 reliably takes place only when blade 12 is distally advanced relative to insert 21. A switch may be provided which, upon actuation of lever 55 in the distal direction, provides power to the electric motor. In this manner the surgeon is able to engage gear 52 and the pinion by merely shifting lever 55 and at the same time switches on electric motor 30.

A drive other than an electric motor also may be provided. What is important is only that the selected drive can engage the instrument in problem-free manner and that it makes possible alternating drives in opposite directions of rotation.

Another difference from the embodiment shown in FIG. 1 is that the instrument in the embodiment of FIG. 5 comprises an ocular 37 at its proximal end, with an adapter 38 fitted to this ocular. In turn, adapter 38 comprises at its proximal end a further ocular 39. The imaging properties of the optics mounted in the insert 21 can be controlled by means of the adapter 38. Illustratively, optics which focuses objects a distance away from objective 25 can be changed by means of the adapter 38 into optics which focuses on the front surface of objective 25. The two imaging possibilities may be selectively toggled by a selecting lever 40. In this manner it is possible to match the instrument especially well to different surgical situations.

What is claimed is:

1. A surgical instrument for creating a tissue canal to seat a sleeve comprising
    a shaft tube having a central axis, a proximal end and a distal end;
    means for rotatably supporting said shaft tube on said instrument;
    a knife blade at said distal end of said tube to form an incision, said blade comprising an axially projecting portion of said distal end of said shaft tube with a sharpened surface for cutting in a circumferential direction of said shaft tube;
    drive means for rotating said shaft tube about a longitudinal axis through a preselected angle and in alternating directions of rotation; and
    an insert mounted in said shaft tube and having a blunt distal end substantially adjacent to said distal end of said shaft tube.

2. An instrument according to claim 1 wherein said preselected angle is adjustable.

3. An instrument according to claim 2 wherein said drive comprises an electric motor and wherein said motor is automatically energized when said blade is axially advanced.

4. An instrument according to claim 1 and further comprising endoscope optics having an objective mounted at said distal end of said insert.

5. An instrument according to claim 3 wherein said optics allows focusing on the front surface of the objective.

6. An instrument according to claim 4 wherein said optics comprises a proximal ocular and focuses on objects spaced beyond said objective, and further comprises an adapter attached to said ocular for adjusting the focal length to enable focusing on the front surface of the objective.

7. Instrument defined in claim 6 wherein said adapter is adjustable in either of two focal lengths for selecting between focusing on the front surface of said objective and at a selected distance beyond said objective.

8. An instrument according to claim 1 and including means for rotatably supporting said insert for rotation about said central axis of said shaft tube.

* * * * *